(12) United States Patent
Vogt

(10) Patent No.: US 7,354,267 B2
(45) Date of Patent: Apr. 8, 2008

(54) TUBULAR ORTHODONTIC ARCH WIRE

(76) Inventor: William Vogt, 3501 Freemansburg Ave., Easton, PA (US) 18045

( * ) Notice: Subject to any disclaimer, the term of this patent is extended or adjusted under 35 U.S.C. 154(b) by 119 days.

(21) Appl. No.: 11/006,555

(22) Filed: Dec. 8, 2004

(65) Prior Publication Data

US 2006/0121406 A1 Jun. 8, 2006

(51) Int. Cl.
*A61C 3/00* (2006.01)
(52) U.S. Cl. .................................................. 433/20
(58) Field of Classification Search .............. 433/20
See application file for complete search history.

(56) References Cited

U.S. PATENT DOCUMENTS

| | | | | |
|---|---|---|---|---|
| 3,878,609 A | | 4/1975 | Wallshein | |
| 4,408,989 A | * | 10/1983 | Cleary | 433/7 |
| 5,017,133 A | * | 5/1991 | Miura | 433/20 |
| 5,092,941 A | * | 3/1992 | Miura | 148/563 |
| 5,344,315 A | | 9/1994 | Hanson | |
| 5,399,088 A | | 3/1995 | Mechley | |
| 5,468,147 A | | 11/1995 | Yao | |
| 5,816,800 A | * | 10/1998 | Brehm et al. | 433/7 |
| 6,062,855 A | * | 5/2000 | Karlin | 433/8 |
| 6,095,809 A | | 8/2000 | Kelly et al. | |

* cited by examiner

*Primary Examiner*—Cris Rodriguez
*Assistant Examiner*—Candice C Stokes

(57) ABSTRACT

A length of tubular material of unitary construction is formed into the approximate shape of a human dental arch for use as an orthodontic arch wire. The tubular material is composed of a super-elastic nickel titanium alloy which may also have shape memory. The cross-sectional shape of the arch wire tube can be round, oval, square, or rectangular. The preferred thickness of the tube is preferably 20 percent of its outside diameter and the tube may be perforated to alter its performance.

9 Claims, 3 Drawing Sheets

TUBULAR ORTHODONTIC ARCH WIRE

FIELD OF THE INVENTION

The present invention relates to orthodontic wires for aligning human teeth. More specifically, it relates to the use of thin-walled tubing having reduced stiffness for use as orthodontic arch wires. Additional modifications may be employed to reduce stiffness further.

BACKGROUND OF THE INVENTION

Orthodontic treatment is the movement of poorly positioned teeth into their correct positions. This treatment usually requires the attachment of bands or brackets to the teeth. In order for the teeth to move, a wire is attached to the brackets or bands through which force can be transmitted to the teeth that need to be straightened.

When the orthodontic bands and brackets are initially attached to malpositioned teeth, a fairly flexible wire shaped in the form of an ideal dental arch is usually placed into the slots and the tubes of the bands and brackets. The arch wire can act as a track to guide the movements of the teeth along the wire when elastic bands or springs are used to supply the force. More often, the arch wire itself acts as the source of the force that moves the teeth because when resilient wires are deflected, they tend to spring back toward their original shape. A wire made from super-elastic metal alloy demonstrates the greatest resilience. Therefore this type of wire is frequently used as the initial wire since it is the most resilient, longest acting, lowest force wire available. In addition, to reduce the amount of force to the lowest amount possible, a wire substantially smaller than the bracket slot is usually used initially in order to have sufficiently reduced stiffness that the wire can be easily placed into the slots of the orthodontic brackets which were placed on the malpositioned teeth. A wire the same size as the orthodontic bracket slot would be too stiff to enter the slot since adjacent slots would be at different angles because the teeth are crooked. Even if it were possible to get this size wire inserted into the brackets, the force would be too great for the orthodontic appliances to withstand and the brackets would break off from the teeth. In addition, at this force level the patient would experience extreme discomfort.

Historically, arch wires were first made from precious metals such as gold. Gold wires were not very effective due to the softness of the metal allowing the wires to deform easily. Later, stainless steel wires were introduced which had increased resilience but also greatly increased stiffness. In an attempt to reduce the high force level of these stainless steel wires, cabled or twisted orthodontic wires were invented. Although the stiffness of the wire was reduced and the resilience increased compared to solid stainless steel wires, the force level was still higher than ideal and the wires still had a tendency to permanently deform when they were moderately stressed. Wires made of super-elastic alloys were introduced that reduced the force level even further. Although multi-stranded super-elastic wires reduce the force compared to solid wires, they are even more prone to breakage and fraying than stainless steel multi-stranded wires. Even after the above inventions, the force level of existing arch wires remains too high for a full-size wire to fully engage the slots of orthodontic brackets without either breaking the brackets off of the teeth or causing extreme patient discomfort.

The larger the cross-section of the wire, the more of the bracket slot that will be filled. When the slot of the orthodontic bracket is filled to its capacity by the largest wire possible, the control over tooth movement is at its greatest. Therefore, the ideal wire is one that is flexible enough that it can be fully engaged into the slot of the bracket without having to place high force levels on it in order to do so. The lighter the force the more comfortable it will be for the patient. There is also some evidence that lighter continuous forces allow the teeth to move more rapidly because heavy forces sometimes cause tissue necrosis. A larger wire with lower force would have the advantage of giving the orthodontist better control while reducing the force applied to the teeth resulting in greater patient comfort.

An orthodontic wire also needs to be highly resistant to permanent plastic deformation so that after it is engaged it can still deliver a force load to the teeth sufficient enough to result in tooth movement. If the wire deforms no force will be delivered to the teeth. To reduce the number of adjustments, the ideal wire should be capable of delivering the ideal force level over a long distance without the force level reducing dramatically.

There have been attempts in the art to provide an arch wire with a lighter continuous force. For example, U.S. Pat. No. 5,344,315 to Hanson discloses a multi-strand arch wire comprising a plurality of wire strands of super-elastic material wrapped helically parallel to one another along the length of the wire. The helical wire may be hollow or include a solid core. U.S. Pat. No. 3,878,609 issued to Wallshein discloses a coiled arch wire configured into a tightly wound helix having an array of successively abutting and substantially parallel turns. U.S. Pat. No. 5,399,088 issued to Mechley discloses a multiple layer wire which includes an outer sheath and an inner core of different metallic compositions. Also, to improve the art, the external cross-sectional configuration of orthodontic arch wires has been modified to reduce stiffness even further. As an example, both U.S. Pat. Nos. 6,095,809 and 5,468,147 describe arch wires with longitudinal grooves extending along the exterior surface in order to increase the flexibility of the wire while maintaining effectively the same outside dimensions. While good in theory, these devices have shown to be impractical.

There is therefore a need in the art for an orthodontic arch wire which provides a lighter engagement force yet has sufficient dimension to completely fill the slots of the orthodontic brackets. There is further need to provide an orthodontic arch wire of reduced force which is feasible to produce, long-lasting, and which provides patient comfort.

SUMMARY OF THE INVENTION

In order to meet the needs in the art of orthodontic arch wires, the present arch wire has been devised. In one embodiment, the arch wire consists of a tubular length of material composed of a super-elastic alloy. Alternate embodiments include tubular lengths of material of different shapes such as round, oval, rectangular, or square. In yet another embodiment of the invention, the tubular arch wire is perforated to further reduce its restorative force.

More specifically, the applicant has invented an orthodontic arch wire comprising a length of tubular material of unitary construction formed into the approximate shape of a human dental arch. The tubular material is composed of a super-elastic nickel titanium alloy which may also have shape memory. The arch wire further includes a tube wall having a thickness of between 7.5 percent to 35 percent of its outside diameter which may be perforated. The thickness is preferably approximately 20 percent of the outside diameter of the tube. The cross-sectional shape of the arch tube can be round, oval, square, or rectangular.

It is therefore the object of the invention to provide a tubular orthodontic material that has the benefit of providing reduced force levels over solid or multi-stranded wires of the same exterior dimensions. Another object is to provide a tube that is capable of providing a consistent continuous force over a long period and over a large range of stress. Another object is to provide round, oval, square, or rectangular shaped tubes in dimensions that allow the tubes to fill the rectangular orthodontic bracket slots as fully as possible. Another object is to devise a tube that provides a fairly consistent force level over a wide range of deflection. Yet another object is to create a tube with perforations in its wall that allow for further reducing the amount of force that is delivered by the tube. Another object is to provide a tube with a smooth outside wall to reduce friction for easier tooth movement. An additional object is to provide a tube that can be compressed in the direction of its cross-sectional dimension and can recover its original shape.

Other objects and advantages of the invention will be apparent to those of skill in the art from the following drawings and description of the preferred embodiment.

DESCRIPTION OF THE PREFERRED EMBODIMENT

Figure 1:
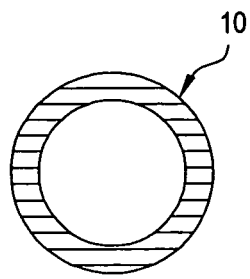
FIG. 1 is a front cross-sectional view.
Figure 2:
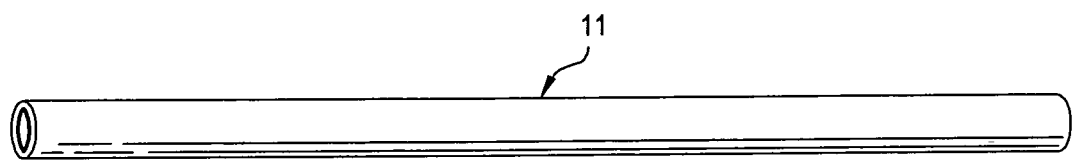
FIG. 2 is a right front isometric view.
Figure 3:
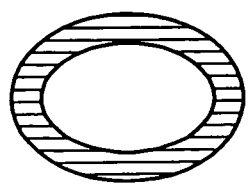
FIGS. 3 and 4 are front cross-sectional views of alternate embodiments.
Figure 4:
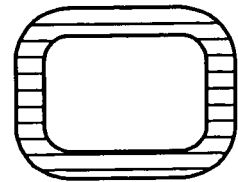

The preferred embodiment is a thin walled tube as is depicted in FIGS. 1 and 2. The tube is preferably made from a super-elastic, shape memory material, preferably nickel titanium alloy that is shaped in the form of a dental arch dimensioned to fit into the bracket slots and tubes of orthodontic appliances. The dimensions range from a round tube with an outside dimension of 0.012-inch diameter to as large as a rectangular tube with outside dimensions of 0.025 by 0.030 inches. The arch tube may be made in different shapes such as but not limited to round as in FIG. 1, oval as seen in FIG. 3, or rectangular as seen in FIG. 4. The tube can easily be manufactured in a round configuration but can later be reshaped through compression and heat treatment into different shapes. Alternatively, a mandrel may be inserted into the tube and the tube heat-treated to change its shape. The tube may have multiple shapes within the same tube such as oval in the middle and round toward the ends.

Figure 5:
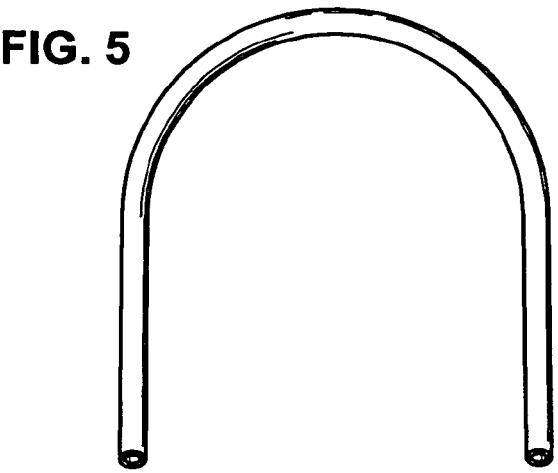
FIG. 5 is a top front isometric view.

Referring still to FIGS. 1 and 2, the arch tube wall 10 is 7.5% to 35% of the outside diameter of the tube in thickness. The preferred wall thickness is approximately 20% of the outside diameter of the tube. If the tube is non-circular the tube wall will be between 7.5% to 35% of the average of the height and thickness of the tube. Because the tube is composed of super-elastic material, the tube will be kink resistant and can be more easily inserted into malaligned teeth without permanently deforming. When the tube is preformed into an ideal dental arch as seen in FIG. 5 and inserted by deforming the wire to engage orthodontic brackets on malaligned teeth, it will straighten those teeth by moving them in such a manner that they will align themselves to the ideal arch form as the wire reverts to its original ideal dental arch shape. It should be understood that the drawings are not necessarily to scale but are meant to be illustrative of the various shapes and configurations of different embodiments of the invention may take.

Figure 6:
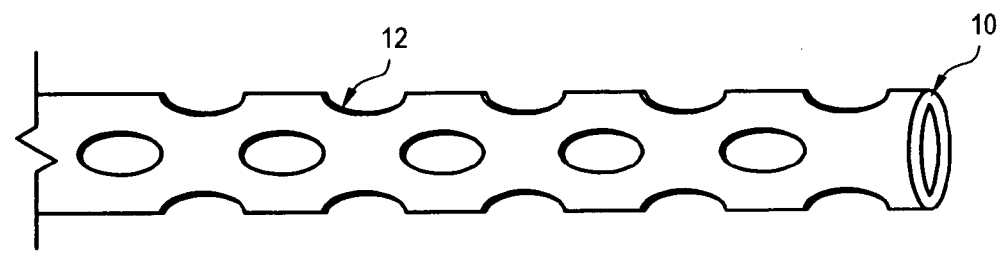
FIG. 6 is a left side isometric partial view of an alternate embodiment.

Because the tube contains less material compared to a solid wire of the same outside dimensions, the force level of the tube compared to a solid wire is reduced. As is seen in FIG. 6, in order to further reduce the force the tube can have even more material removed from it by creating perforations 12 of various shapes in the tube wall 10.

Figure 7:
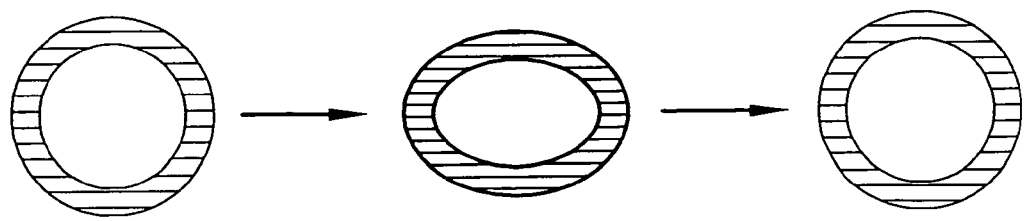
FIG. 7 is a series of sequential front cross-sectional views showing elastic deformation and recovery.
Figure 8:
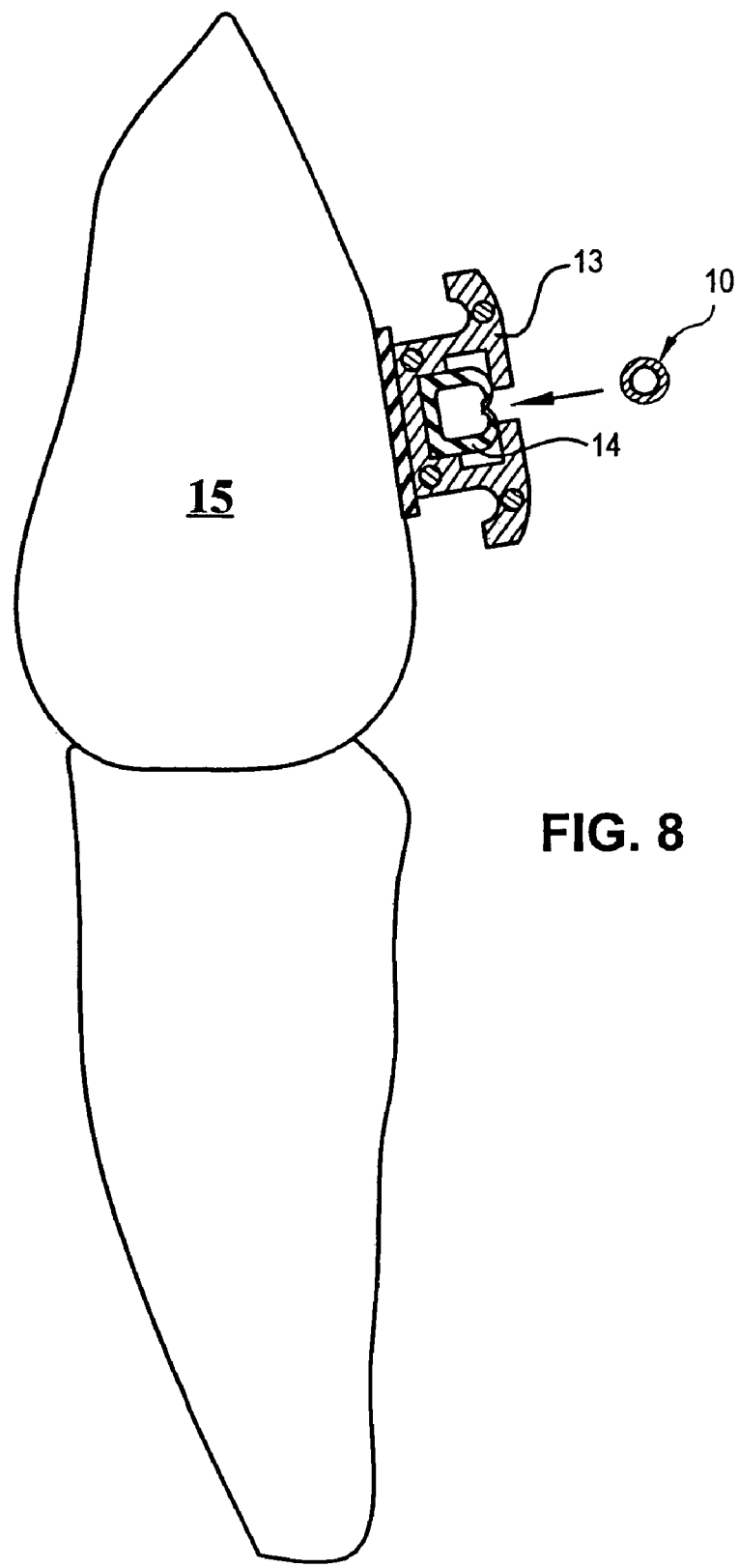
FIG. 8 is a side sectional view.

Referring now to FIGS. 7 and 8, when inserted into a latching orthodontic bracket, the wire will deform laterally as demonstrated in FIG. 7, from round to oval and then back to round as the tubular wire recovers its initial shape. As shown in FIG. 8, latching bracket 13 is affixed to tooth 15. As the arch tube is inserted into the latch 14 of the bracket 13, it can temporarily elastically deform into an oval shape as it slides into the bracket slot. Once engaged, it can elastically regain its original round shape. This allows for easier insertion and removal of the wire. The process is reversed for disengagement of the tube from the bracket. For this application, the outside walls 11 may be highly polished in order to decrease friction and further facilitate the engagement of the tubes into the latching brackets.

It should be understood that there may be other modifications and changes to the present invention that will be obvious to those of skill in the art from the foregoing description, however, the present invention should be limited only by the following claims and their legal equivalents.

What is claimed is:

1. An orthodontic arch wire, comprising:
an arch wire being a length of tubular material substantially non-shapable at room temperature and in the approximate shape of a human dental arch and further including means attachable to a tooth engaging said arch wire, wherein diametrically opposing sidewalls being on opposite sides of a longitudinal axis of said tubular arch wire are radially compressed and deformed when manually applied against said means engaging said arch wire and being self-recovering to their initial shape after the lateral compressive force is removed.

2. The arch wire of claim 1 wherein said tubular material is composed of shape memory material.

3. The arch wire of claim 1 wherein the cross-sectional shape of said arch wire tube is oval.

4. The arch wire of claim 1 wherein the cross-sectional shape of the tube is square.

5. The arch wire of claim 1 in which said tubular material is composed of a super-elastic material.

6. The arch wire of claim 5 wherein said material is composed of a nickel titanium alloy.

7. The arch wire of claim 5 further including a tube wall having a thickness of between 7.5 percent to 35 percent of its outside diameter.

8. The arch wire of claim 7 wherein said wall thickness is approximately 20 percent of the outside diameter of the tube.

9. The arch wire of claim 7 wherein said tube wall is perforated with a plurality of laterally extending holes along its length.

* * * * *